US005557261A

United States Patent [19]
Barbour

[11] Patent Number: 5,557,261
[45] Date of Patent: Sep. 17, 1996

[54] ICE MONITORING AND DETECTION SYSTEM

[75] Inventor: Blair A. Barbour, Madison, Ala.

[73] Assignee: Nichols Research Corporation, Huntsville, Ala.

[21] Appl. No.: 238,886

[22] Filed: May 6, 1994

[51] Int. Cl.$^6$ ................................................. G08B 19/02
[52] U.S. Cl. ..................... 340/580; 340/583; 250/341.8; 250/342; 244/134 F; 348/61
[58] Field of Search ................................... 340/580, 583; 356/50, 51; 244/134 F; 250/255, 341.8, 342; 348/143, 61

[56] References Cited

U.S. PATENT DOCUMENTS

| | | | |
|---|---|---|---|
| 2,359,787 | 1/1942 | Peters | 356/51 |
| 4,054,255 | 10/1977 | Magenheim | 244/134 F |
| 4,274,091 | 6/1981 | Decker | 340/583 |
| 4,604,612 | 8/1986 | Watkins | 340/582 |
| 4,690,553 | 9/1987 | Fukamiza | 356/50 |
| 4,775,118 | 10/1988 | Daniels | 340/580 |
| 5,180,122 | 1/1993 | Christian | 244/134 F |
| 5,218,206 | 6/1993 | Schmitt | 340/583 |
| 5,243,185 | 9/1993 | Blackwood | 340/583 |

Primary Examiner—John K. Peng
Assistant Examiner—Albert K. Wong
Attorney, Agent, or Firm—John C. Garvin, Jr.; Harold W. Hilton

[57] ABSTRACT

An ice monitoring and detection system for determining the presence and thickness of ice on a surface is provided. The system includes an imaging device which includes at least one lens for providing image signals of the surface. The imaging device is operable in a predetermined portion of the electromagnetic spectrum. Image signals from the surface are polarized into discrete polarization changes responsive to the camera receiving image signals proportional to amplitude modulated signals generated by the presence of ice. A processor is provided for converting the modulated signals into discrete polarization changes and for obtaining the difference between the discrete polarization changes which is proportional to the amount of ice on the surface. An indication device provides an output corresponding to the difference between the discrete polarization changes. The difference is indicative of the presence and amount of ice on said surface.

13 Claims, 8 Drawing Sheets

ICE MONITORING AND DETECTION SYSTEM

FIELD OF THE INVENTION

The invention relates to an ice monitoring and detection system (IMADS) for detecting ice on a surface. In particular, the invention is directed to method and apparatus for detecting the presence, location and thickness of ice on aircraft, road surfaces, or the like by the use of polarized imaging techniques.

BACKGROUND OF THE INVENTION

Ice on aircraft wings or other aircraft surfaces is a serious problem because it disturbs the laminar airflow across these surfaces and could result in loss of aerodynamic lift. Likewise, the presence of ice on roads is a serious problem because, as is well known, icy road conditions can cause vehicular accidents which could result in serious injury or death to the vehicle operator or others.

There are numerous systems known in the art to detect ice on a surface such as, for example, an aircraft surface or a road surface. Ice detectors for aircraft are disclosed in U.S. Pat. No. 2,359,787 issued to M. F. Peters, et al. on Oct. 10, 1944 for "Ice Detector"; U.S. Pat. No. 4,054,255, issued to Bertram Magenheim on Oct. 18, 1977; U.S. Pat. No. 4,604,612, issued to Watkins, et al. on Aug. 5, 1986 for "Ice Detector"; U.S. Pat. No. 4,775,118 issued to James W. Daniels on Oct. 4, 1988 for "Ice Detecting System"; and U.S. Pat. No. 5,180,122 issued to Donald J. Christian, et al. on Jan. 19, 1993 for "Apparatus For Deicing".

Some road surface ice detector systems are disclosed in U.S. Pat. No. 4,274,091 issued to Peter W. Decker on Jun. 16, 1981 for Road Surface Ice Detector and Method for Vehicles; and, U.S. Pat. No. 4,690,553 issued to Hiroski Fukamiza, et al. on Sep. 1, 1987 for "Road Surface Condition Detection System".

None of the above identified patents disclose the use of an imaging device (camera) in combination with polarizer means to detect the presence and thickness of ice on a surface.

The present invention is directed to both passive and active ice detection systems for monitoring and detecting the presence and thickness of ice on a surface.

The ice detection system of the present invention measures the polarization changes introduced by the polarizing characteristics of the hexagonal crystals of ice. The polarization may be linear, elliptical, depolarized or circular. As is well known, there are several sources of polarized light in a polarization image of a surface which contains ice. The strongest source of polarization lies in the fact that ice emits radiation according to Fresnel's law. Fresnel's law describes the quantity of emitted polarized light in the planes parallel and perpendicular to the plane of emission as a function of the angle of emission. The angle of emission is defined as the angle between the normal to the surface and the angle at which the surface is being viewed. The plane of emission is defined as the plane containing the normal of the surface and the angle of emission. The difference in the quantity of light emitted in the planes parallel and perpendicular to the plane of emission results in linearly polarized, emitted light.

A second source of polarization in ice lies in the fact that ice is a naturally occurring birefringent crystal. Birefringence is a material property that selectively changes the speed of light depending upon its state of polarization. A retardation or phase change results from the different speeds of light for light composed of particular polarization states propagating in ice. The phase change transforms light of one polarization state into another, from linear to elliptical for example. Birefringence is also introduced in ice crystals by stress and strain in the formation of the ice.

A third source of polarization lies in the multiple reflections and refractions that light undergoes in leaving the ice crystal. A source of depolarization lies in the air bubbles, impurities, and grain boundaries of polycrystalline ice. Each of these sources of polarization gives rise to the distinctive polarization signature of ice that differentiates it from the underlying surface.

The present invention exploits these facts and provides both a passive and active ice measurement system each of which can use any of several types of cameras, which facilitate measurement of the emittance or reflection of radiation from the ice and other surrounding surfaces. The key to ice detection system is the ability to very precisely measure by means of a polarization device, the polarization changes introduced on the background signature by the presence of ice. The basic system is comprised of a state-of-the-art camera system with integrated polarization means.

Both the active and passive system use a camera designed to collect images of the scene or area of interest, a polarization device that varies these images while images are collected in a memory device, a processor to process the collected images, and a display to display the processed images to the operator. The camera also includes a lens and a sensitive focal plane array (FPA). Different lens configurations as well as zoom lenses are required dependent upon the application. The polarization device (such as a linear polarizer) is placed behind the camera lens and in front of the focal plane array (FPA).

The polarization device can take the form of a linear polarizer, which as stated hereinbelow, may be one of many forms such as polaroid material, a wire grid, Wollaston prism, or Brewster plates.

As stated hereinbelow an electrically controllable retarder such as liquid crystal variable retarder may also be used. The retardation device may also be rotated.

The polarization device provides the means by which the polarization state of the light incident on the FPA is determined. Depending on the elements of the polarizing device, one or all polarization states can be characterized. One common embodiment of the polarizing device is a rotating linear polarizer.

The polarization device introduces a modulation of the background measurement whose amplitude is related to the amount of polarized radiation emitted or reflected by the ice. The polarization device can be varied in a step wise fashion or varied in a continuous fashion that is synchronized with the frame rate of the camera to produce a modulated signal. For example, if the polarizer is a linear polarizer rotating at a frequency of 3 revolutions per second (RPS) a camera with a 30 Hertz frame rate would produce a 3 Hertz signal based upon the various amplitude measurements made at 36 degree increments. The rotation of the polarizer creates an amplitude modulation in the areas of the image where the emitted radiation is polarized.

It is, therefore, an object of the present invention to provide a system for detecting ice on a surface.

It is another object of the present invention to provide such a system which is a passive real-time ice detection system.

It is still another object of the present invention to provide such a system which is an active ice measurement system.

It is yet another object of the present invention to provide such an ice detection system wherein imaging in combination with a polarizer, is used to not only detect ice on the surface but to provide actual indications of the thickness of the ice.

These and other objects of the present invention will become more readily apparent from the following description and drawing.

PASSIVE SYSTEM

The IMADS passive real-time ice detection system of the present invention measures the differential amplitude of the polarization introduced by the birefringent characteristics of the hexagonal asymmetric crystals formed in ice. The detection device can use any of several types of cameras, which facilitate measurement of the emittance of radiation from the ice and other surrounding surfaces. The key to a passive system is the ability to very precisely measure the modulation introduced on the background signature by a polarizer. The basic system is comprised of a state of the art camera system with integrated polarizer means.

The system uses a camera designed to image the area of interest. Different lens configurations as well as zoom lens are available dependent on the application. In one embodiment of the imaging device of the present invention, a polarizer is placed behind the camera lens and in front of a sensitive focal plane array (FPA) and the polarizer is rotated by the use of a motor and encoder along with drive belt to rotate the polarizer at a constant modulation or by phase control in the motor drive electronics. The polarizer has a home (zero) position and encoder to precisely determine the polarizer orientation at the time each measurement was made. The polarizer rotation introduces a modulation of the background measurement whose amplitude is related to the amount of polarized radiation emitted or transmitted through ice. The motor can be toggled between angular positions or rotated at a precise rotation rate. The rotation rate of the motor will be synchronized with the frame rate of the camera to produce a modulated signal at the polarizer rotation frequency. For example, if the polarizer is rotating at a frequency of 3 revolutions per second (RPS) a camera with a 30 Hertz frame rate would produce a 3 Hertz signal based upon the various amplitude measurements made at 36 degree increments. The rotation of the polarizer creates an amplitude modulation in the areas of the image where the emitted radiation is polarized.

A frame of signals from the camera is measured and stored in a first buffer with the polarizer positioned at a specified orientation. The polarizer is then rotated to a second orientation and a second frame of data is measured and stored in a second buffer. A portion of the radiation from the ice will have a preferred polarization orientation. The radiation from the surrounding contrasting surfaces will have no preferred polarization orientation. The processor will then compute the difference between these frames of data to determine the polarization fraction. The polarization fraction is then biased at a level appropriate to eliminate noise and background and placed in an overlay buffer which is combined with the live video to create a pseudo or false color in locations where ice has been detected. The overlay buffer is used to indicate the presence of ice and is colored for display only.

The remaining portion of the system (which includes temperature control means, automatic gain circuitry, power module and control panel) is a commercial off the shelf (COTS) thermal imaging system. The IMADS system is not concerned with the temperature difference between the ice and the surrounding surface or the difference in the emissivity of the surfaces. The IMADS sensor detects the difference between the amount of polarized light received from the ice (birefringent crystal) and the surrounding surfaces. The camera is able to passively detect the radiation emitted from the surfaces.

ACTIVE SYSTEM

The IMADS active ice measurement system of the present invention utilizes the same components as described in conjunction with the passive system but also uses an active source of illumination (such as a laser, for example) to illuminate the area of interest. It is well known that ice is a naturally occurring birefringent crystal which selectively changes the speed of light (dependent upon its state of polarization) as the radiation is transmitted through it. The amount of the transmission speed change (retardation) is a function of the ice thickness. For example, a single linear polarization state will be transformed from linear to elliptical to circular depending on the ice thickness. A system could be comprised of a camera with an integrated polarizer and a source of polarized radiation configured to measure the amount of retardation introduced by the transmission of the polarized radiation through or reflected by the surface (or material) being examined.

Phase retardation is dependent on the birefringence of the crystal. The change in the polarization state can be monitored by mapping the detected intensity levels of the radiation passing through the ice as the polarizer is rotated in front of the camera. Relative intensity is a function of retardation angle and the polarizer orientation. A variation in the intensity seen through the polarizer is indicative of the change in the thickness of the crystalline structure.

The present IMADS ice measurement system exploits these facts. Areas where no ice is present are suppressed by placing the polarizer at the complimentary angle to the illumination polarization. As ice forms the polarization state is transformed from linear to elliptical. This transformation is detected as an increase in the intensity of radiation passing through the polarizer. A point will be reached where the phase has changed by 180° and will again be suppressed. This fact causes the image of the region ice to have dark and light bands and are used to determine the thickness variations.

In a similar manner, as discussed above, a polarizer is placed behind the lens and in front of a focal plane array and is rotated by the use of a motor and drive belt or by a phase control motor to change the polarizer orientation at a constant frequency. The polarizer has a home (zero) position sensor to indicate the zero angle position. The motor can be toggled between angular positions or rotated at a precise rotation rate. The rate will be a multiple of the framing rate of the camera. For example, if the camera has a framing rate of 30 Hertz then the polarizer would be rotated at a minimum of 3 revolutions per second (RPS) which would correspond to 10 frames per revolution or a frame every 36 degrees of polarizer rotation. The polarizer orientation angle change between frames needs to be optimized for the specific application.

The remaining portion of the system (as discussed supra) is a commercial off the shelf (COTS) camera system. This is an active IMADS which detects the phase retardation and amplitude variations to determine the presence and thickness of the ice.

In another embodiment of the imaging device of the present invention a filter, such as a notch filter is placed in circuit between the processor and threshold circuit to lock on to the AC modulation which occurs as a result of the separation states of the polarizer due to the rotation thereof. By locking on to the AC modulations the ice locations within the image is locked onto.

In still another embodiment of the imaging device of the present invention a rotating polarizer is not used thereby eliminating the need for the motor, belt, motor controller and the "home" position sensor. In this embodiment lens means are provided to direct first and second image signals from the surface being observed in discrete paths to each of a pair of stationary polarizers (which are polarized in different polarization planes). After being polarized in different planes these image signals are directed in different paths to first and second focal plane arrays. The focal plane arrays convert the image signals into electrical signals, a portion of which is directed to a monitor in the form of live video signals, and the remaining portion thereof which are sent to first and second buffer means. The difference between the signals received in each buffer is determined as discussed above and a signal corresponding to the difference is transmitted to an overlay buffer which injects this signal into the live video circuit of the monitor.

The different paths for the first and second image signals may be generated by using a pair of lens mounted in a single housing wherein each lens receives images from the surface. The lens may be mounted in a single housing or in separate housings. Alternatively, a single lens may be used in conjunction with a beam splitter (mirrors, etc.) to receive image signals from the single lens and direct these image signals in two discrete paths to an associated polarizer and focal plane array. If desired, a pair of cameras may be used along with the appropriate circuitry (including the buffers described above) to focus on the surface under observation.

BRIEF DESCRIPTION OF THE DRAWINGS

FIGS. 8a and 8b are diagrammatic views illustrating the polarization discrimination process in accordance with the principles of the present invention. FIG. 8a illustrates the position of the polarizer when the polarizer is in a first predetermined state of polarization. FIG. 8b illustrates the position of the polarizer when the polarizer is in a second predetermined state of polarization.

DESCRIPTION OF THE PREFERRED EMBODIMENTS

Figure 1:
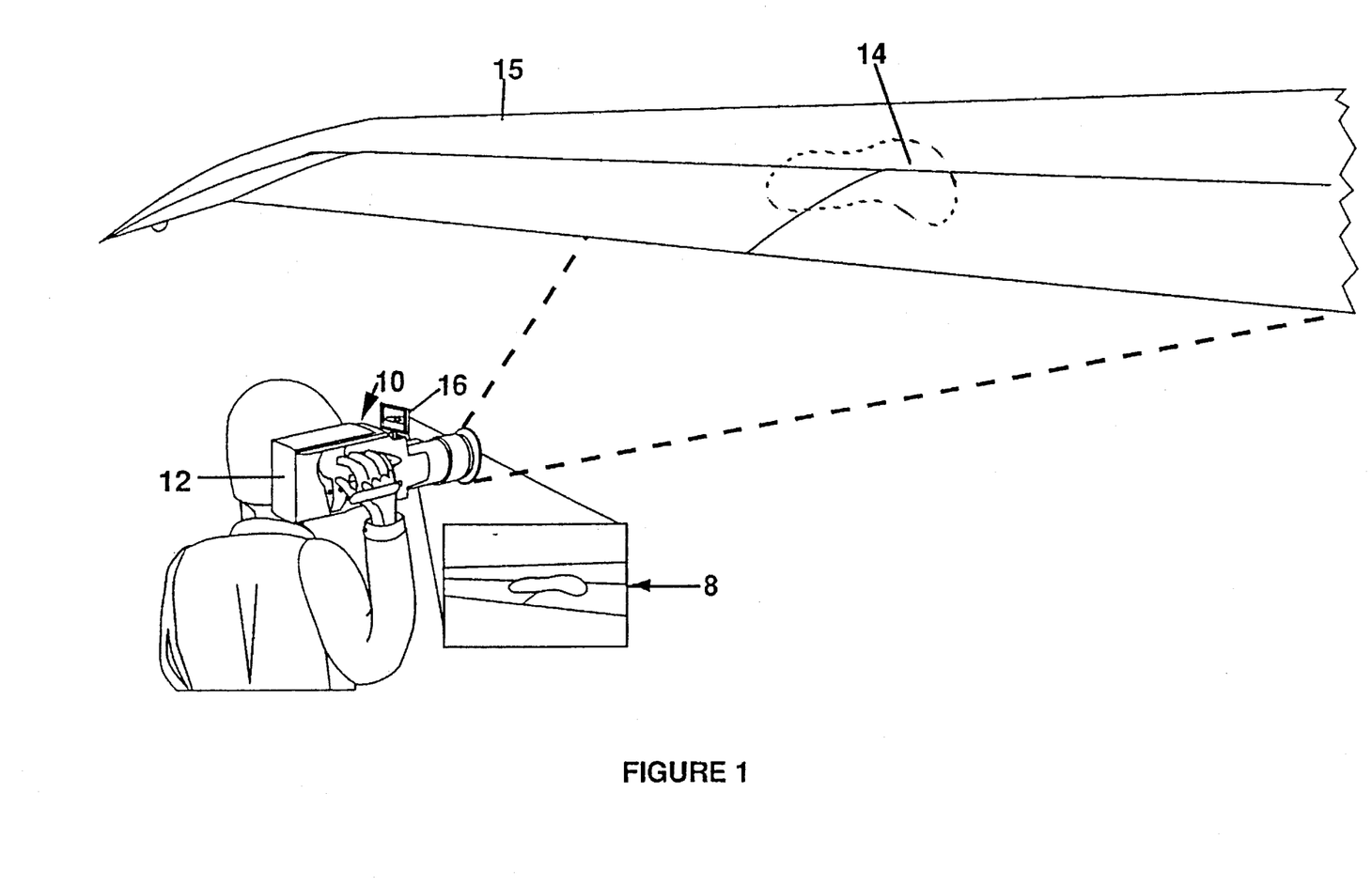
FIG. 1 is a pictorial view illustrating a passive embodiment of the ice monitoring and detection system of the present invention being used to detect ice on surfaces of an aircraft.

As seen in FIGS. 1, a passive ice monitoring and detection system 8 is shown to include a camera 10 and a camera housing 12. The camera is shown as being focussed on an iced surface 14 on the wing 15 of an aircraft. A monitor 16 is illustrated as being mounted on the housing 12 of imaging device 10 to provide a visual indication to an operator of the ice conditions on the surface of the aircraft. While the imaging device is shown to be carried on the shoulder of an individual this is for illustrative purposes only, and it is to be understood that other means of supporting the imaging device may be resorted to that is within the spirit and scope of the present invention. For example, the imaging device may be mounted in the towers typically found at airports, or to a vehicle which may be driven to the vicinity of the aircraft. Such vehicle may be provided with an elevatable platform for support of the camera thereon. In the case of monitoring roads for ice thereon, a helicopter may be provided to serve as a support for the camera or the camera may be mounted to a vehicle or bridge as discussed hereinbelow.

Figure 2:
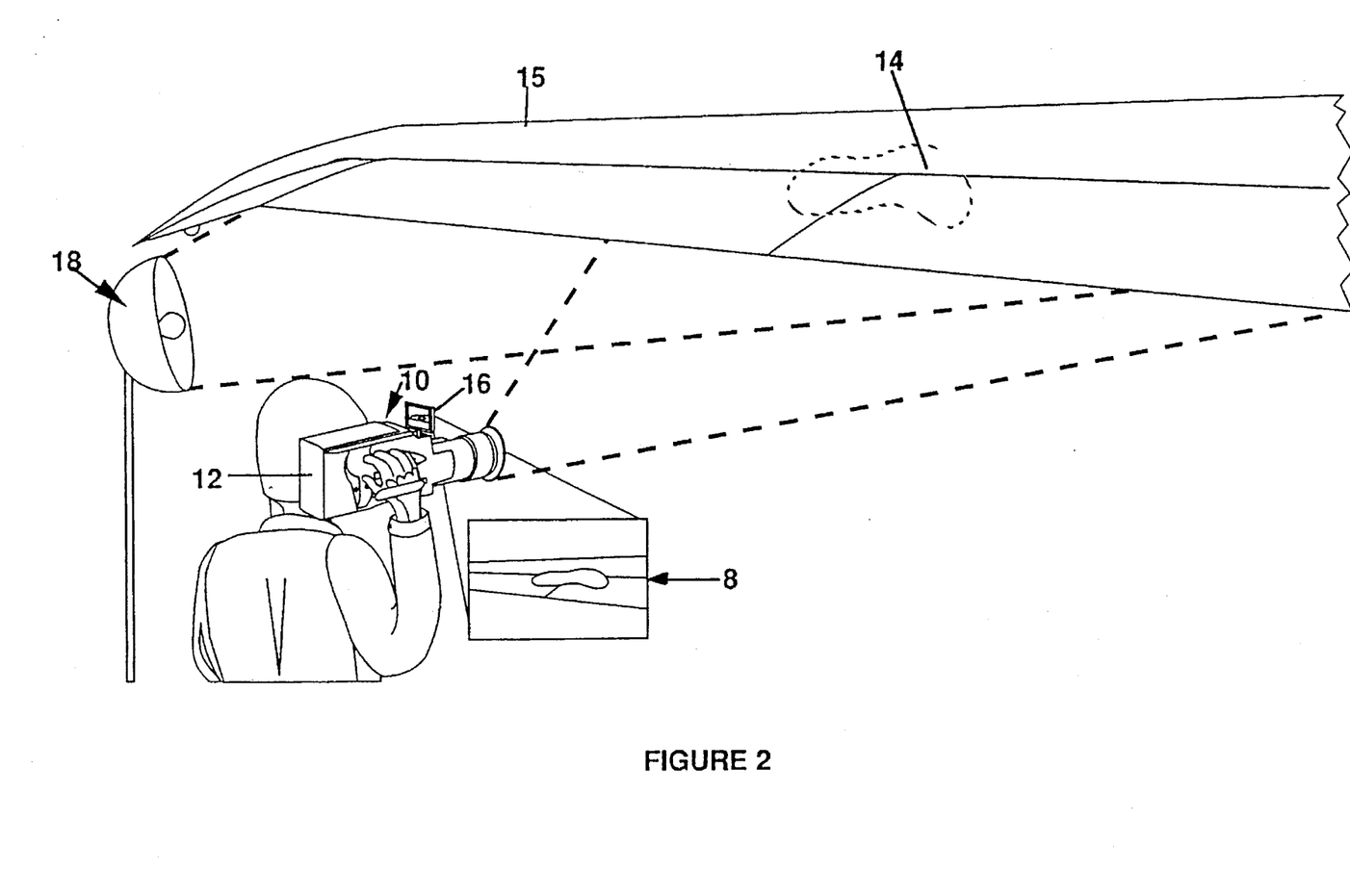
FIG. 2 is a pictorial view similar to FIG. 1 of an active ice monitoring and detection system utilizing the principles of the present invention.

FIG. 2 is a view similar to FIG. 1 but also discloses an illuminator 18 for illuminating the ice surface to therefore define an active ice detection system. (The illuminator may be a laser, for example.) All other elements of the active system remain as shown in FIG. 1 wherein like reference numerals refer to like parts.

Figure 3:
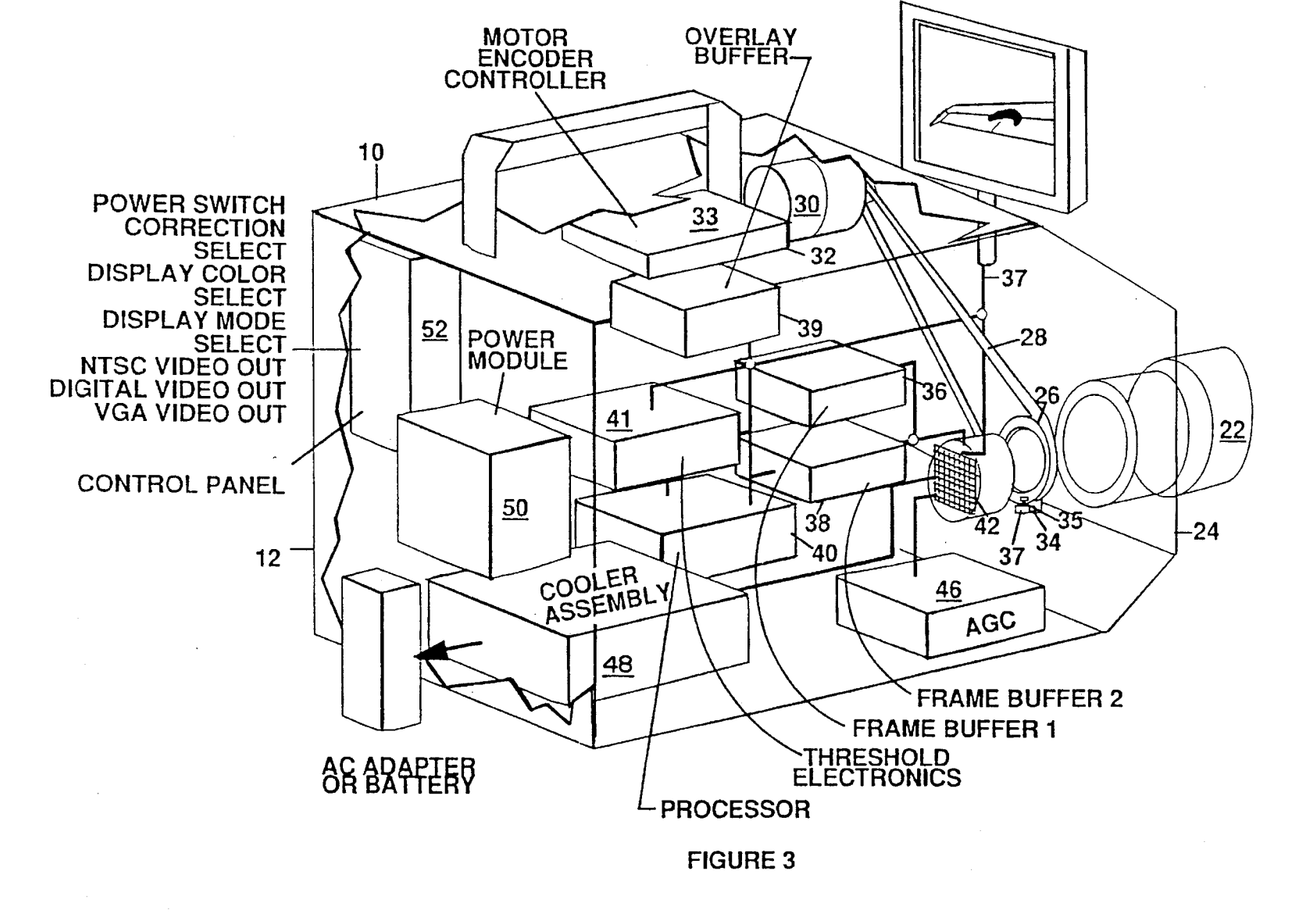
FIG. 3 is a diagrammatic pictorial view partially broken away of an imaging device used in the ice monitoring and detection system of the present invention.
Figure 4:
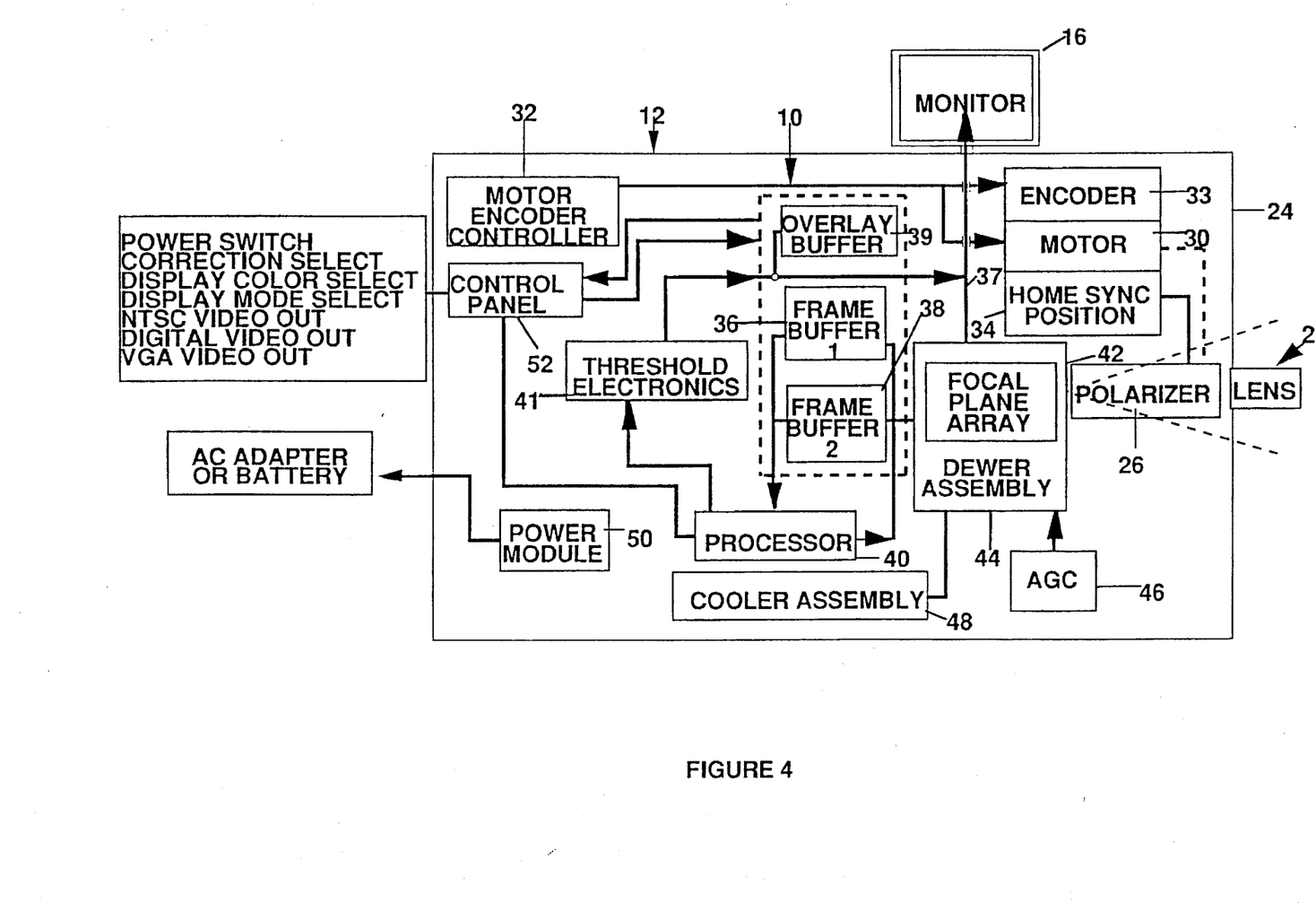
FIG. 4 is a block diagram of the structure of FIG. 3.

The camera or sensor 12 of one embodiment of the present invention is illustrated in the pictorial diagrammatic view (FIG. 3) and in the block diagram (FIG. 4). As seen in FIGS. 3 and 4 the camera 10 of the ice monitoring and detection system 8 in shown to include housing 12 which supports an iris lens 22 at the forward portion 24 thereof. The housing 12 is shown as enclosing a polarizer 26, which is rotated by a motor 30 driven by a belt 28 (FIG. 3) which is controlled and monitored by a motor encoder controller 32 and a motor encoder 33. A "home" sync position sensor 34 is provided for synchronization of the rotatable polarizer as will be discussed hereinbelow. A pair of frame buffers 36 and 38 are provided to receive signals from successive frames generated in the camera and a processor 40 is provided to process the frame differences. A threshold circuit 41 is provided for eliminating background noise. The housing 12 further encloses a focal plane array 42, a dewar assembly 44 (FIG. 4), an automatic gain circuit 46, a cooler assembly 48 (including hybridized control and dewar refrigeration circuitry), a power module 50 and control panel 52 (which includes a power switch, a correction select switch, a display color select, a display mode select, a NTSC video out port, a digital video out port, and a variable graphics adapter (VGA) video out port. Each of the components numbered 44–52 of the above described system is found in commercial thermal imaging systems.

In operation, data from the camera is passed in sequence into frame buffer 36 and frame buffer 38. The processor 40 controls the assignment of the data to the respective frame buffers and then performs real time analysis to determine the presence and thickness of the ice. The processor includes circuitry to detect amplitude modulated signals from the surface which is passed on to the overlay buffer (such amplitude detection circuits are well known in the art). The frame buffers are standard memory chip buffers. The polarization is thresholded by standard threshold means in the threshold electronics circuitry 41 for limiting the levels which get sent to an overlay buffer 39. Thresholding is used for the purpose of eliminating the background noise effects. The threshold portion of the signal which gets passed to the overlay buffer is the detected ice region. The overlay is superimposed over the live image which is transmitted via the sensor 42 to the monitor as indicated by line 37 in FIG. 3. This superimposed image indicates to the observer the specific location at which the ice is detected.

The home sync position sensor 34 may include a nonferrous member 35 which is mounted on the periphery of the polarizer 26 and a proximity sensor 37 which is mounted adjacent to the rotatable polarizer to determine the orientation of the polarizer as it is rotated past the sensor 37.

Figure 5:
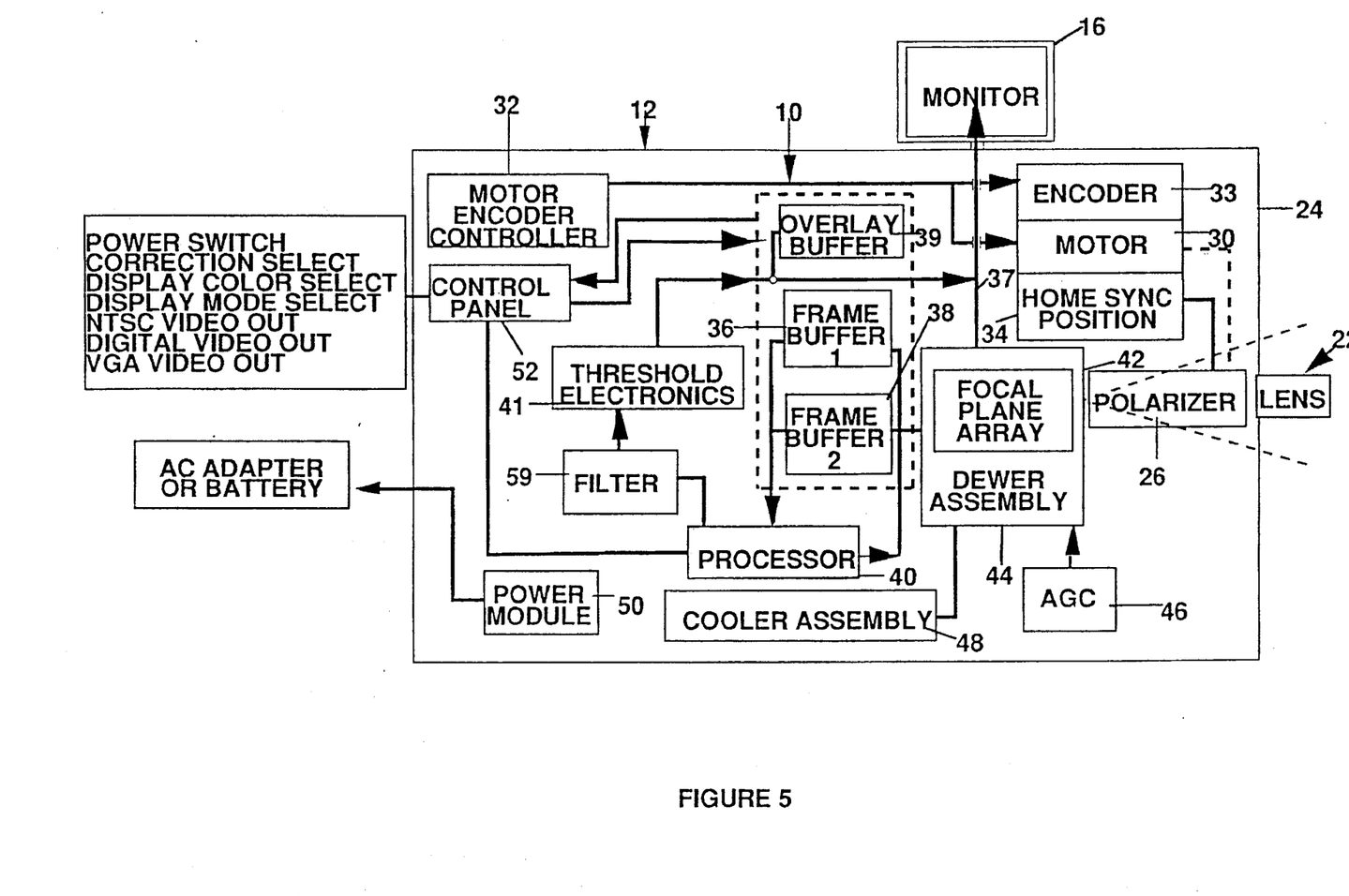
FIG. 5 is a view similar to FIG. 4 and illustrates the use of a filter in circuit with the threshold circuit and processor to lock on the AC modulation component generated by the presence of ice on the surface.

In the embodiment shown in FIG. 5, wherein like reference numerals refer to like parts, a filter 59 (notch filter, for example) is provided in circuit between processor 40 and threshold circuitry 41 to provide AC modulation coupling with the rotational rate of the polarizer by locking onto the AC rotational rate of the polarizer. Such modulation occurs as a result of the separation states of the polarizer.

Figure 6:
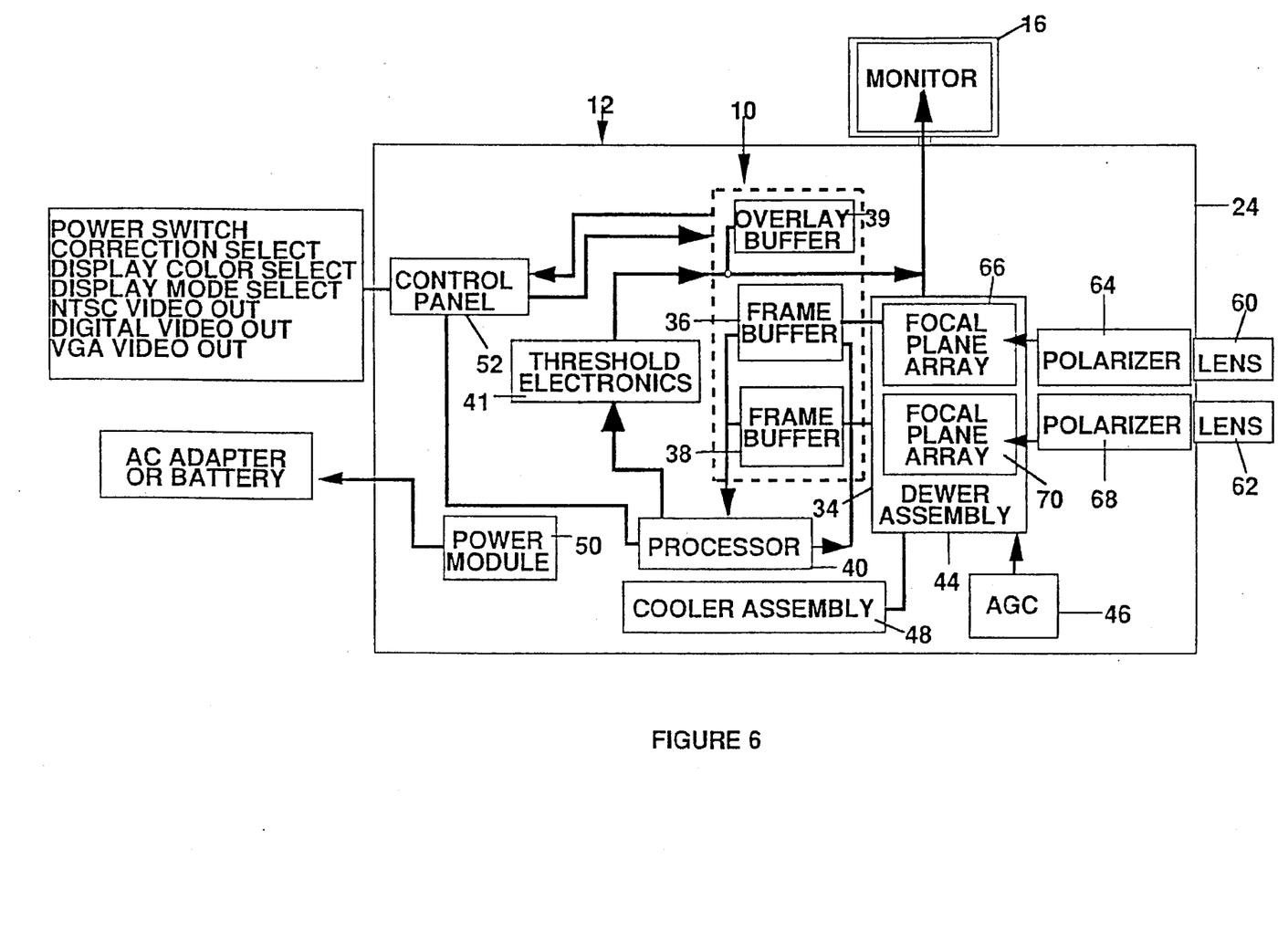
FIG. 6 is a view similar to FIG. 4 and illustrates a block diagram of an embodiment of the present invention which uses a pair of lens to receive image signals from the surface and to direct these image signals in two different paths to an associated polarizer and focal plane array.

FIG. 6 illustrates another embodiment of the camera of the present invention wherein like reference numerals refer to like parts. In this embodiment two lens 60 and 62 receive image signals from the surface under observation. Lens 60 directs the image signals to a polarizer 64, which polarizes the image signals in a first polarization plane, and then onto a focal plane array 66 which then directs an electrical signal which is indicative of the polarization of the polarizer 64 to frame buffer 36.

Lens 62 directs the image signals from the surface to a polarizer 68 and then onto a focal plane array 70 which then directs an electrical signal, which is indicative of the differently polarized polarizer 68 to frame buffer 38.

After the signals are received by buffers 36 and 38 from the focal plane arrays 64 and 68, they are then processed in the manner described above.

Figure 7:
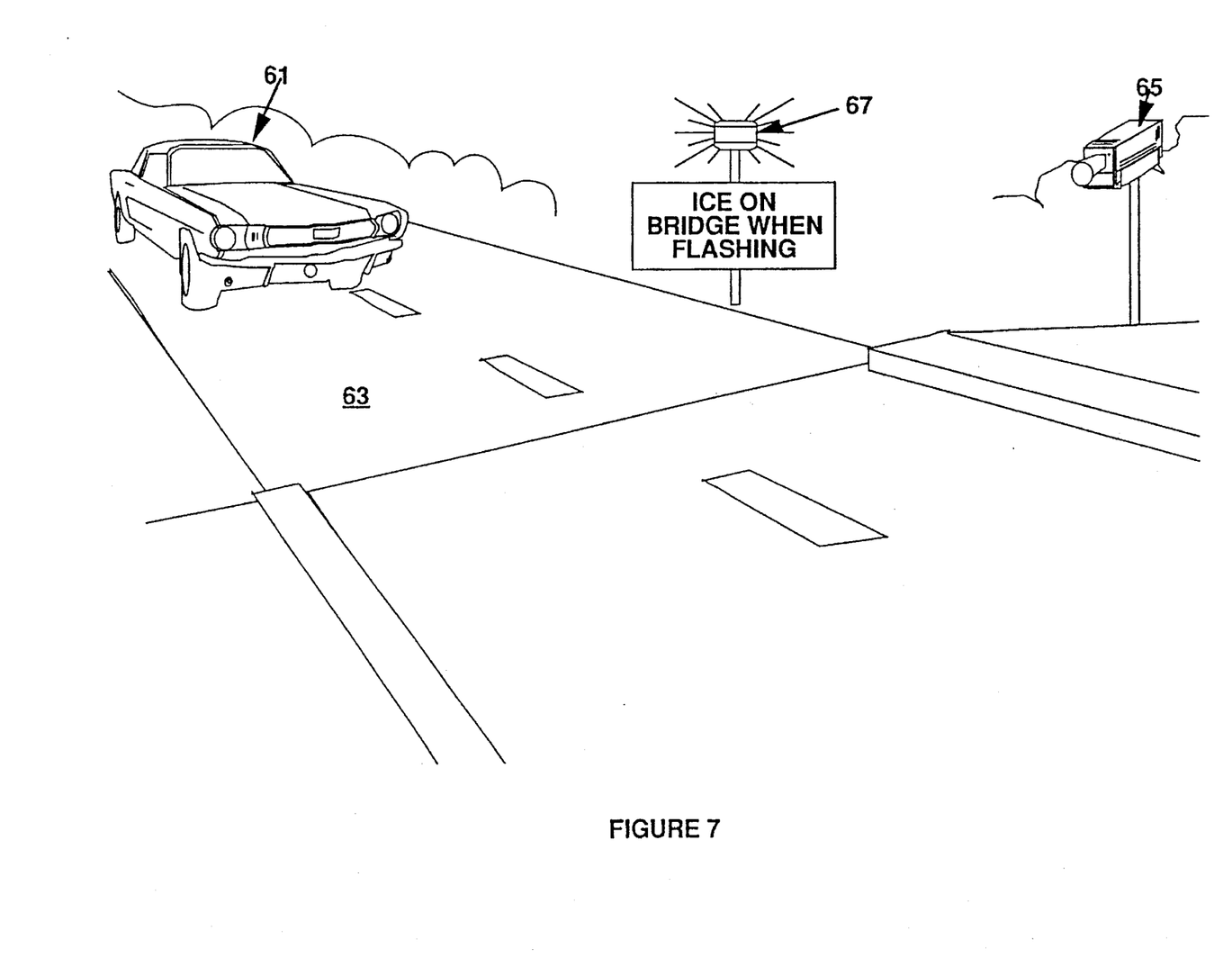
FIG. 7 is a pictorial view of one ground based system for monitoring a road surface for the presence of ice.

As seen in FIG. 7, a ground based system is shown to include a vehicle 61 traveling on a road surface 63. A roadway monitoring system 65 (which may be either the passive or active system described above) is positioned adjacent a portion of the road (which may be a bridge, for example) to detect the presence of ice on the road. The monitoring system 65 includes electrical circuitry (not shown) to illuminate a safety warning system 67 in the vicinity of the road to warn the operator of the vehicle of the presence of ice. No visual monitor (screen) is required in this application.

Figure 8A:
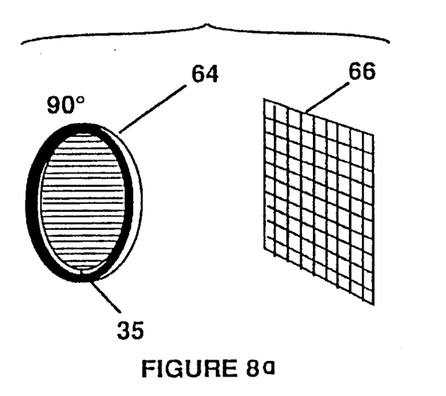
Figure 8B:
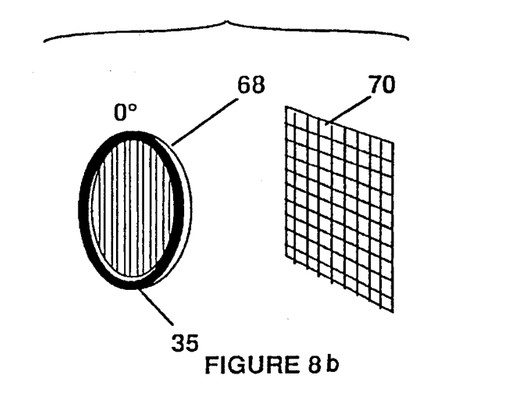

FIGS. 8a and 8b are diagrammatic views illustrating the relative positions of the polarizers of FIG. 6 during the polarization discrimination process. FIG. 8a illustrates the position of the polarizer relative to the lens 64 and the FPA 66 when data are sent to the processor. FIG. 8b illustrates the position of polarizer 68 relative to lens 62 and FPA 70 when data are sent to the processor.

Figure 9:
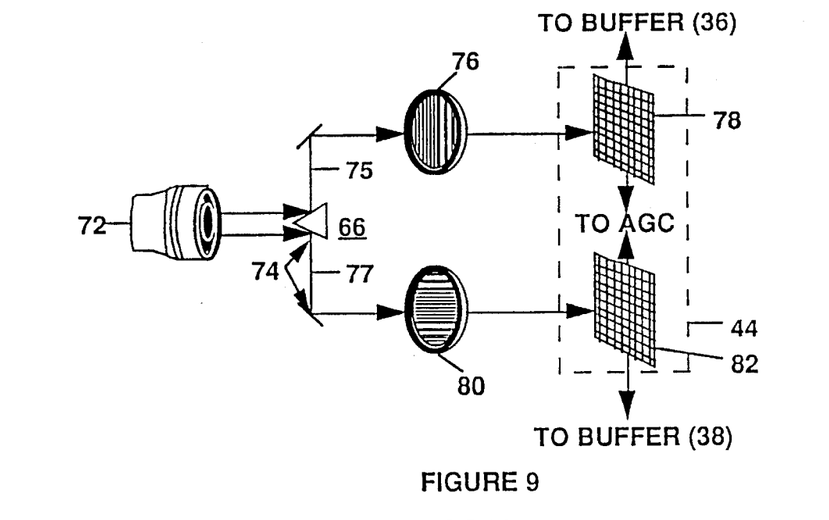
FIG. 9 is a diagrammatic view of an embodiment of the invention which utilizes a single lens in combination with beam splitter means which directs image signals from the surface under study to an associated polarizer, focal plane array, frame buffer and appropriate circuitry as shown in FIG. 6.

FIG. 9 illustrates another embodiment of the present invention wherein the reference numerals refer to like parts. As seen in FIG. 9, a single lens 72 directs image signals to a beam directing means 74 (mirrors, beam splitters, etc., for example), which then directs the image signals in two paths 75 and 77 to a first polarizer 76 and then onto a corresponding focal plane 78. The electrical signals generated in the focal plane array 78 are then directed to buffer 36.

In like manner, the signals from lens 72 is directed in path 77 to a second differently polarized polarizer 80 and then onto a corresponding focal plane array 82. The electrical signals generated in focal plane array 82 are then sent on to buffer 38.

After the signals are received by buffers 36 and 38 from the focal plane array 78 and 82 they are processed in the manner described above.

Figure 10:
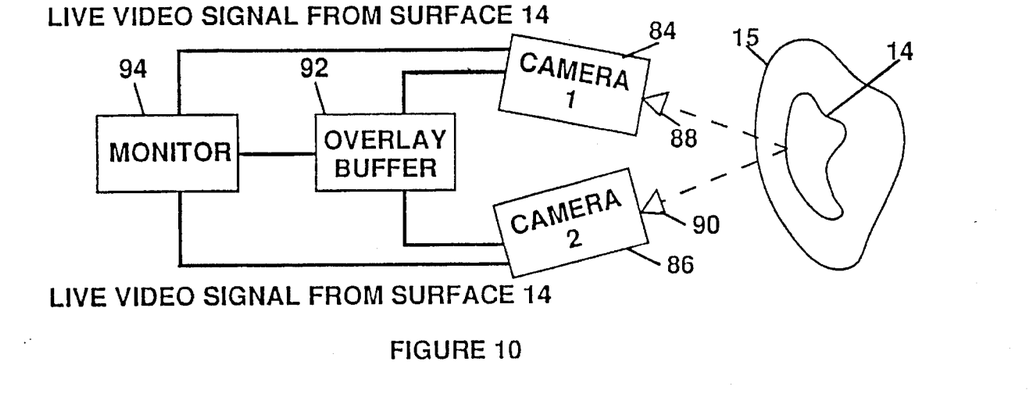
FIG. 10 is a diagrammatic view of an embodiment of the present invention which utilizes a pair of cameras and associated lens. An overlay buffer is provided to receive signals from the respective frame buffers, focal plane arrays and appropriate circuitry as shown in FIG. 6.

FIG. 10 is another embodiment of the imaging system of the present invention wherein like reference numerals refer to like parts. In this embodiment a pair of cameras 84 and 86 are provided with their own lens 88 and 90 to provide the image signals in different paths as in FIG. 6. All of the remaining components are as in FIG. 6 wherein each lens transmits the image signals to a corresponding polarizer, focal plane array and buffer. FIG. 10, however, illustrates the use of a single overlay buffer 92 (instead of each camera having an individual overlay buffer). Buffer 92 receives the overlay signals from each camera and directs the overlay signal, along with live video signals to a single monitor 94.

It is to be understood that the imaging device may be any of many types of imaging devices, such as, infrared focal plane arrays, forward looking infrared images, thermal viewers, charged coupled device cameras, intensified cameras, raster scan cameras, vidicon cameras, charge detection devices which may use interline transfer and line scan cameras.

It is to also be understood that the polarization device may be any of many types of polarizers, such as, wire grid, polaroid, dichroic, thin film stacks, birefringent prisms (Nicol, Glan-Thompson, Wollaston and Rochon), scattering plates, brewster plates, retarders, prezo-electric, and liquid crystal retarders.

Furthermore, it is to be understood that the type of lens and focal plane arrays (FPA) may be chosen for the particular application of the system. For example, the lens and FPA may be chosen to operate in the infrared, ultraviolet or visible portions of the spectrum. Preferably, the passive system would utilize an infrared lens and infrared FPA system while the active system would use a lens and FPA compatible with either the infrared, ultraviolet or visible portions of the spectrum.

Although the present invention has been described in connection with specific forms and embodiments thereof, it is to be appreciated that various modifications other than these discussed above may be resorted to that is within the spirit and scope of the invention as defined in the appended claims. One such modification would be the use of two cameras and two focal plane arrays, for example.

I claim:

1. A system for detecting the presence and thickness of ice on a surface, said system including video recording means having a framing rate, said video recording means disposed for providing a live image of said surface to a monitor for display thereof, said video recording means including:

a housing having a lens therein for receiving electromagnetic radiation emanating from said surface, said electromagnetic radiation defining an image of said surface;

filter means for filtering the received said radiation, wherein said filter means outputs filtered radiation that is a function of polarization of the received radiation;

means for rotating said filter means at a rate of rotation which is a multiple of said framing rate whereby said filter means outputs radiation that is a function of polarization of the received radiation and said rate of rotation of said filter means;

sensor means for receiving said filtered radiation and converting said filtered radiation into first and second electrical signals which are proportional to a multiple of the framing rate of said video recorder means;

first buffer means for receiving and storing said first electrical signals which are indicative of a frame of signals produced when said polarizer is in a first orientation;

second buffer means for receiving and storing said second electrical signals which are indicative of a succeeding frame of signals produced when said polarizer is in an orientation other than said first orientation;

means for computing the difference between said first and second electrical signals and for providing an output which is a polarization fraction signal representative of ice appearing on said surface;

overlay buffer means for receiving and storing said polarization fraction signal and for providing said polarization fraction signal as an input to said monitor, whereby an overlay image is superimposed over said live image on said monitor to indicate the presence of ice in said image on said monitor.

2. Apparatus as in claim 1 wherein said sensor means is a focal plane array.

3. Apparatus as in claim 2 wherein said filter means is a single rotatable polarizer element.

4. Apparatus as in claim 3 including a motor and means for controlling rotation thereof, said motor being operatively coupled with said polarizer for the rotation thereof.

5. Apparatus as in claim 4 wherein said means for controlling the rotation of said motor is a motor encoder for controlling the rate of rotation and determining the orientation of said motor.

6. Apparatus as in claim 5 including a polarizer home position sensing means for sensing and indicating the zero boresight position of said polarizer means.

7. Apparatus as in claim 3 including a discrete source of radiation for illuminating said surface.

8. A system for detecting the presence and thickness of ice on a surface, said system including video recording means for providing a live image of said surface on a monitor for display thereof, said video recording means including:

a housing having a lens therein for receiving electromagnetic radiation emanating from a surface, said electromagnetic radiation defining an image of said surface;

means for directing said received radiation in two different paths;

a first polarizer element disposed in a first said path and a second polarizer disposed in a second said path, said polarizers having their plane of polarization in different states of polarization;

first and second focal plane arrays respectively associated with said first and second polarizer elements to receive polarized images therefrom and to convert said images to polarized image signals indicative of said polarized images;

first buffer means for receiving and storing said polarized image signals from said first focal plane array;

second buffer means for receiving and storing said polarized image signals from said second focal plane array;

means for determining the difference between polarized image signals resulting from the different states of polarization of said polarizer elements;

means for converting said difference to an output signal from said first and second buffer means which serves as an input to said monitor for producing a pseudo image of said ice on said surface in said image displayed by said monitor.

9. Apparatus as in claim 8 wherein said lens means is a single lens, and said video recording means is provided with image directing means to direct said image in said two paths to said two focal plane arrays.

10. Apparatus as in claim 8 wherein said lens means is a pair of lens for directing said image signals in two different paths to said two focal plane arrays.

11. Apparatus as in claim 10 including a discrete source of illumination for illuminating said surface.

12. The method of determining the presence and thickness of ice on a surface and displaying an image of said ice on a video monitor as an overlay on a live video image of said surface comprising the steps of:

video recording electromagnetic radiation emanating from said surface, said electromagnetic radiation defining an image of said surface;

filtering the received radiation in a filter means and providing an output signal therefrom which is a function of polarization of said received radiation;

sensing said filtered radiation and providing output signals proportional to different states of polarization of said filter means:

processing said sensed signals to determine the difference therebetween;

providing an output signal indicative of said differences; and providing said output signal as an input into said live image to produce a pseudo-image of ice on said live image of said surface.

13. A system for detecting the presence and thickness of ice on a surface, said system including video recording means for having a framing rate, said video recording means displayed for providing a live image of said surface to a monitor for display thereof, said video recording means including:

a housing having a lens therein for receiving electromagnetic radiation emanating from said surface, said electromagnetic radiation defining an image of said surface;

a single polarizer for polarizing the received said radiation;

means for rotating said single polarizer at a rate of rotation which is a multiple of said framing rate;

sensor means for receiving said polarized radiation and converting said polarized radiation in to first and second electrical signals which are proportional to the framing rate of said video recorder means;

first buffer means for receiving and storing said first electrical signals which are indicative of a frame of signals produced when said polarizer is in a first orientation;

second buffer means for receiving and storing said second electrical signals which are indicative of a succeeding frame of signals reduced when said polarizer is in an orientation other than said first orientation;

means for computing the difference between said first and second electrical signals and for providing an output which is a polarization fraction signal representative of ice appearing on said surface.

* * * * *